(12) United States Patent
Fuerst et al.

(10) Patent No.: US 12,369,771 B2
(45) Date of Patent: Jul. 29, 2025

(54) APPARATUS, SYSTEMS, AND METHODS FOR INTRAOPERATIVE VISUALIZATION

(71) Applicant: Verb Surgical Inc., Santa Clara, CA (US)

(72) Inventors: Bernhard Adolf Fuerst, Mountain View, CA (US); Berk Gonenc, Cupertino, CA (US); Risto Kojcev, Cupertino, CA (US); Pablo Garcia Kilroy, Menlo Park, CA (US); Benjamin Sanker, San Jose, CA (US); Felix Bork, Schnuerpflingen (DE)

(73) Assignee: Verb Surgical Inc., Santa Clara, CA (US)

( * ) Notice: Subject to any disclaimer, the term of this patent is extended or adjusted under 35 U.S.C. 154(b) by 0 days.

(21) Appl. No.: 18/412,773

(22) Filed: Jan. 15, 2024

(65) Prior Publication Data
US 2024/0225418 A1    Jul. 11, 2024

Related U.S. Application Data

(63) Continuation of application No. 18/046,794, filed on Oct. 14, 2022, now Pat. No. 11,910,997.
(Continued)

(51) Int. Cl.
*A61B 1/00*      (2006.01)
*A61B 90/00*     (2016.01)
(Continued)

(52) U.S. Cl.
CPC ...... *A61B 1/00045* (2013.01); *A61B 1/00009* (2013.01); *A61B 1/00027* (2013.01);
(Continued)

(58) Field of Classification Search
CPC ............ A61B 1/00045; A61B 1/00009; A61B 1/00027; A61B 1/00055; A61B 90/361;
(Continued)

(56) References Cited

U.S. PATENT DOCUMENTS 7,317,955 B2   1/2008   McGreevy
7,688,889 B2   3/2010   Krause
(Continued)

FOREIGN PATENT DOCUMENTS

JP    2007-136209 A    6/2007

OTHER PUBLICATIONS

Buzz Virtual, Extra & Ordinary, Delivering extraordinary integration, 2022, Brainlab AG, 6 pages.
(Continued)

*Primary Examiner* — Kyu Chae
(74) *Attorney, Agent, or Firm* — Aikin & Gallant, LLP

(57) ABSTRACT

Errors in a blended stream that would result in non-display or obscuring of a live video stream from a medical device may be automatically detected, and a failover stream corresponding to the first live video stream may be displayed to medical personnel. For example, one or more second input streams that are being blended may contain no data or invalid data which may result in the blended stream not displaying (or obscuring) the live video stream (if the blended were displayed). Switching from blending to a failover buffer may occur within the time to process a single video image frame. Upon detection (prior to display) that the blended stream would not display the live video stream, display of the live video stream from the failover buffer may be initiated. Other aspects are also described and claimed.

20 Claims, 9 Drawing Sheets

Related U.S. Application Data

(60) Provisional application No. 63/256,514, filed on Oct. 15, 2021.

(51) Int. Cl.
  H04N 19/59     (2014.01)
  H04N 21/2187   (2011.01)
  H04N 21/431    (2011.01)
  H04N 21/81     (2011.01)

(52) U.S. Cl.
  CPC ........ *A61B 1/00055* (2013.01); *A61B 90/361* (2016.02); *H04N 19/59* (2014.11); *H04N 21/2187* (2013.01); *H04N 21/4312* (2013.01); *H04N 21/8146* (2013.01)

(58) Field of Classification Search
  CPC .......... A61B 2090/371; A61B 1/00039; A61B 1/00043; A61B 1/00006; A61B 1/000094; A61B 1/000095; A61B 1/0004; A61B 1/0005; A61B 90/37; H04N 19/59; H04N 21/2187; H04N 21/4312; H04N 21/8146; H04N 21/431; H04N 21/42653; H04N 21/44008
  See application file for complete search history.

(56) References Cited

U.S. PATENT DOCUMENTS

| | | | |
|---|---|---|---|
| 8,086,008 | B2 | 12/2011 | Coste-Maniere et al. |
| 10,610,310 | B2 | 4/2020 | Todd et al. |
| 10,863,230 | B1* | 12/2020 | Pham ................. H04N 21/6547 |
| 11,910,997 | B2* | 2/2024 | Fuerst ................... A61B 90/37 |
| 2007/0165141 | A1 | 7/2007 | Srinivas et al. |
| 2007/0211930 | A1 | 9/2007 | Dolwick et al. |
| 2009/0036902 | A1 | 2/2009 | DiMaio et al. |
| 2011/0282140 | A1 | 11/2011 | Itkowitz et al. |
| 2011/0298814 | A1 | 12/2011 | Mathew et al. |
| 2017/0143429 | A1* | 5/2017 | Richmond ............. A61B 34/37 |
| 2017/0333275 | A1 | 11/2017 | Itkowitz et al. |
| 2019/0200844 | A1 | 7/2019 | Shelton, IV et al. |
| 2020/0053335 | A1 | 2/2020 | Casas |
| 2020/0093357 | A1 | 3/2020 | Scott et al. |
| 2020/0246081 | A1 | 8/2020 | Johnson et al. |
| 2020/0322516 | A1 | 10/2020 | Doser et al. |
| 2020/0374491 | A1* | 11/2020 | DeAngelus ............ G06V 10/22 |
| 2021/0382559 | A1 | 12/2021 | Segev et al. |
| 2022/0104822 | A1 | 4/2022 | Shelton, IV et al. |
| 2023/0248452 | A1* | 8/2023 | Levine ................. A61B 90/361 600/114 |
| 2023/0316545 | A1* | 10/2023 | Liu ........................ G06V 20/48 382/103 |

OTHER PUBLICATIONS

Notice of Allowance for U.S. Appl. No. 18/046,794, dated Oct. 4, 2023.

PCT/IB2022/059862, "PCT Notification of Transmittal of the International Search Report and the Written Opinion of the International Searching Authority, or the Declaration", mailed Dec. 30, 2022, 9 pages.

Non-Final Office Action received for U.S. Appl. No. 18/046,903, mailed Mar. 13, 2025, 15 pages.

Extended European Search Report received for European Patent Application No. 22880524.8, mailed May 27, 2025, 13 pages.

* cited by examiner

APPARATUS, SYSTEMS, AND METHODS FOR INTRAOPERATIVE VISUALIZATION

CROSS-REFERENCE TO RELATED APPLICATIONS

This application is a continuation of U.S. application Ser. No. 18/046,794, filed Oct. 14, 2022, which claims the benefit of U.S. Provisional Patent Application No. 63/256,514, filed on Oct. 15, 2021, which are incorporated herein by reference.

FIELD

The subject matter disclosed herein relates to intraoperative visualization and specifically to apparatus, systems, and methods that enhance fault tolerance in intraoperative visualization systems.

BACKGROUND

Visualization systems are often used intraoperatively for imaging tissue, performing biopsies, surgery, diagnostic, and/or other medical procedures. The term "intraoperative" as used herein refers to actions performed or events that occur during any medical procedure (invasive or non-invasive). In situations where a visualization system mixes and blends multiple streams, unexpected failures may result in no image being shown to medical personnel. Because visualization is often central to the performance of many medical procedures, failures can detrimentally impact performance of the procedure causing delays, increasing the likelihood of errors, interrupting flow, lowering device utilization, and in some cases could lead to the procedure being aborted. Accordingly, some embodiments disclosed herein enhance safety and efficacy by enhancing fault tolerance in intraoperative visualization systems.

SUMMARY

In some embodiments, a method may comprise: receiving, one or more graphics streams with an alpha channel, wherein the graphics streams comprise one or more graphics frames; receiving at least one first intraoperative live video stream comprising live video frames, the at least one first intraoperative live video stream being received from a medical device; storing at least one current graphics frame into a first buffer; blending the at least one current graphics frame from the first buffer with the at least one current live video frame into at least one blended frame; and initiating, in real-time during the intraoperative procedure, display of current live video frame, in response to a contemporaneous determination that the blending would result in non-display of the at least one current live video frame. In some embodiments, the at least one first intraoperative live video stream may be obtained by mixing two intraoperative live video streams. In some embodiments, the at least one first intraoperative live video stream may comprise a stereoscopic live video stream.

In some embodiments, the method above may further comprise displaying, in real time, the at least one current live video frame along with an error indication.

In some embodiments, the determination to initiate display of the current live video frame may occur within the time to complete the blending of the at least one current graphics frame with the at least one current live video frame. In some embodiments, the determination to initiate display of the at least one current live video frame may be based on a ratio of a number of solid lines in the at least one blended frame to a total number of lines in the at least one blended frame. For example, the determination to initiate display of the at least one current live video frame may be made when the ratio exceeds a threshold.

In some embodiments, a display of the at least one blended frame may be initiated, in response to a determination that the blending would result in display of the at least one current live video frame. For example, the determination to initiate display of the at least one blended frame may be made when the ratio of a number of solid lines in the at least one blended frame to a total number of lines in the at least one blended frame does not exceed a threshold.

In some embodiments, receiving at least one first intraoperative live video stream may comprise at least one of: optionally storing the at least one current live video frame into at least one second buffer; or downsampling the at least one current live video frame and storing the at least one downsampled current live video frame into at least one third buffer; or a combination thereof. In some embodiments, the downsampling may be performed in real-time.

In another aspect, an apparatus may comprise: at least one memory, the memory comprising a plurality of buffers, and a processor coupled to the memory wherein the processor is configured to: receive, one or more graphics streams with an alpha channel, wherein the graphics streams comprise one or more graphics frames; receive at least one first intraoperative live video stream comprising live video frames, the at least one first intraoperative live video stream being received from a medical device; storing at least one current graphics frame into a first buffer; blend the at least one current graphics frame from the first buffer with the at least one current live video frame into at least one blended frame; and initiate, in real-time during the intraoperative procedure, display of current live video frame, in response to a contemporaneous determination that the blending would result in non-display of the at least one current live video frame. In some embodiments, the at least one first intraoperative live video stream may be obtained by mixing two intraoperative live video streams. In some embodiments, the at least one first intraoperative live video stream may comprise a stereoscopic live video stream. In some embodiments, the apparatus and/or the processor may be configured to perform the methods described above.

In a further aspect, a system may comprise: means for receiving, one or more graphics streams with an alpha channel, wherein the graphics streams comprise one or more graphics frames; means for receiving at least one first intraoperative live video stream comprising live video frames, the at least one first intraoperative live video stream being received from a medical device; means for storing at least one current graphics frame into first buffering means; means for blending the at least one current graphics frame from the first buffering means with the at least one current live video frame into at least one blended frame; and means for initiating, in real-time during the intraoperative procedure, display of current live video frame, in response to a contemporaneous determination that output of blending means would result in non-display of the at least one current live video frame. In some embodiments, the robotic medical system may include means to perform the methods described herein.

In a further aspect, a system may comprise: at least one memory, the memory comprising a plurality of buffers, and a processor coupled to the memory wherein the processor is configured to: receive, one or more graphics streams with an alpha channel, wherein the graphics streams comprise one or more graphics frames; receive at least one first intraoperative live video stream comprising live video frames, the at least one first intraoperative live video stream being received from a medical device; storing at least one current graphics frame into a first buffer; blend the at least one current graphics frame from the first buffer with the at least one current live video frame into at least one blended frame; and initiate, in real-time during the intraoperative procedure, display of current live video frame, in response to a contemporaneous determination that the blending would result in non-display of the at least one current live video frame. In some embodiments, the at least one first intraoperative live video stream may be obtained by mixing two intraoperative live video streams. In some embodiments, the at least one first intraoperative live video stream may comprise a stereoscopic live video stream. In some embodiments, the apparatus and/or the processor may be configured to perform the methods described herein.

In some embodiments, a computer-readable medium may comprise instructions to configure a processor to: receive, one or more graphics streams with an alpha channel, wherein the graphics streams comprise one or more graphics frames; receive at least one first intraoperative live video stream comprising live video frames, the at least one first intraoperative live video stream being received from a medical device; storing at least one current graphics frame into a first buffer; blend the at least one current graphics frame from the first buffer with the at least one current live video frame into at least one blended frame; and initiate, in real-time during the intraoperative procedure, display of current live video frame, in response to a contemporaneous determination that the blending would result in non-display of the at least one current live video frame. In some embodiments, the at least one first intraoperative live video stream may be obtained by mixing two intraoperative live video streams. In some embodiments, the at least one first intraoperative live video stream may comprise a stereoscopic live video stream. In some embodiments, computer-readable medium may comprise instructions to configure the processor to perform the methods described herein.

BRIEF DESCRIPTION OF THE DRAWINGS

Embodiments of the invention will be described, by way of example only, with reference to the drawings.

Figure 1:
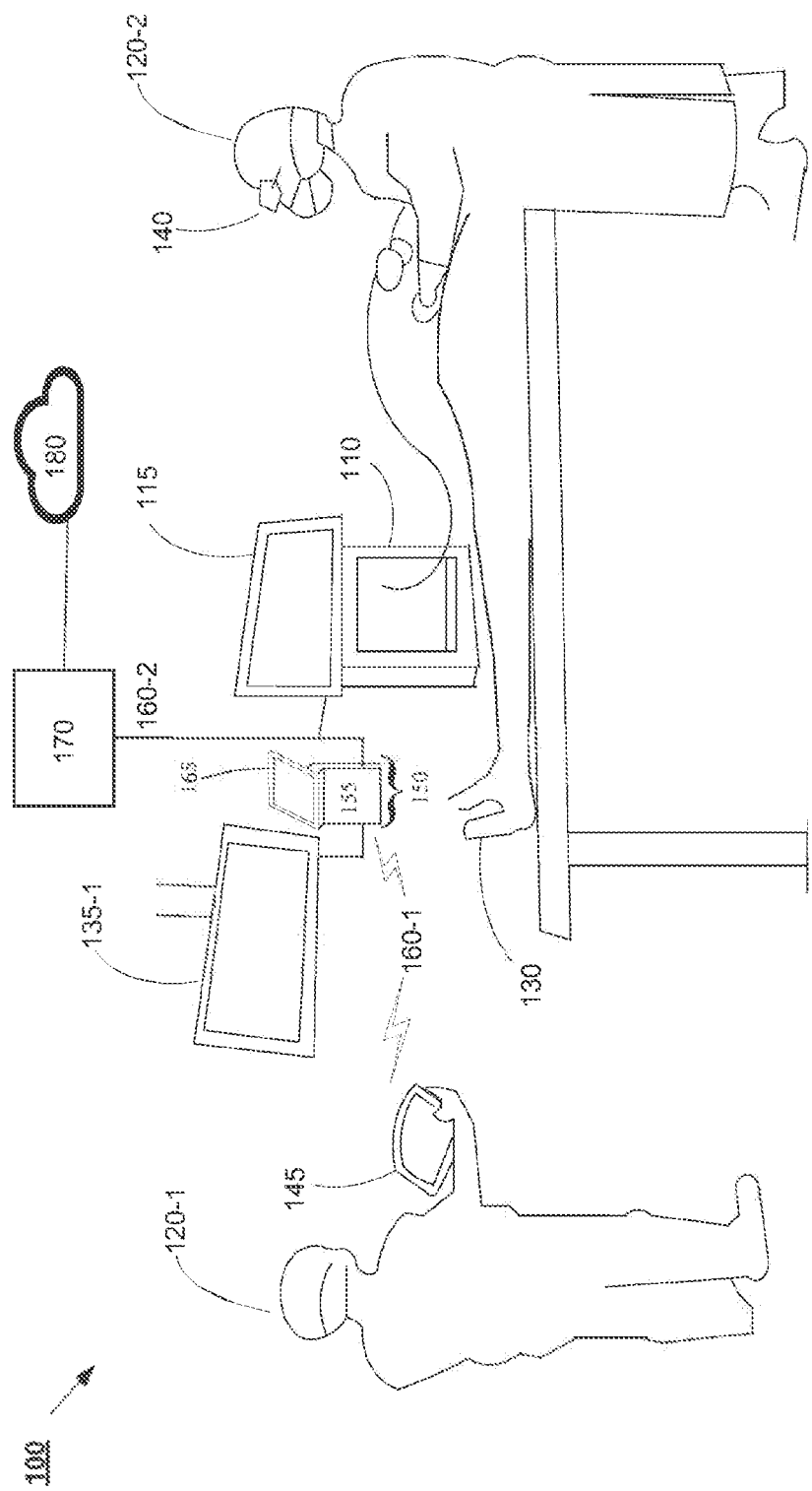
FIG. 1 shows an example diagram illustrating an example system for intraoperative visualization in accordance with certain embodiments disclosed herein.

Like reference numbers and symbols in the various figures indicate like elements, in accordance with certain example embodiments. In addition, multiple instances of a functional element may be indicated by following a first number for the element with a letter or with a hyphen and a second number. For example, multiple instances of an element 160 may be indicated as 160-1, 160-2, 160-3 etc. When referring to such an element using only the first number, any instance of the element is to be understood (e.g., element 160 in the previous example would refer to elements 160-1, 160-2, and/or 160-3).

DETAILED DESCRIPTION

Some disclosed embodiments pertain to apparatus, systems, and methods to facilitate intraoperative visualization. In some embodiments, inputs from multiple graphics and video streams may be received. The graphics streams may include instrument sensor data, robot information and parameters (e.g., during robot-assisted surgery), information provided by an Artificial Intelligence (AI) engine, which may be based on analysis of stored data (e.g., gathered during prior intraoperative procedures), etc. The information provided by the AI engine may include intraoperative guidance, suggestions, warnings, and/or assistance. In some embodiments, the AI information may be provided in the form of augmentations (e.g., using augmented reality (AR) techniques over an intraoperative video stream). The video streams may include preoperative images, intraoperative medical images, video obtained by a medical device (such as an endoscope) during the intraoperative procedure, and/or video from operating room cameras, graphics associated with a user interface, etc. In some embodiments, one or more of the intraoperative video streams may be blended (e.g., using alpha blending or a-blending) with one or more graphics streams and displayed to medical personnel (e.g., a surgeon) on one or more of a monitor, headset, and/or a portable computing device to facilitate performance of the intraoperative procedure. For clarity, the live video obtained intraoperatively by a medical device (such as the endoscope) being used for performance of a medical procedure is also referred to herein as the first live video stream or first intraoperative live video stream. The terms "composite stream" or "blended stream" are used to refer to result of blending the first live video stream and graphics streams.

In some embodiments, errors in the blended stream that would result in non-display or obscuring of the first live video stream may be automatically detected, and a failover stream corresponding to the first live video input stream may be displayed to medical personnel. For example, one or more second input streams that are being blended may contain no data or invalid data (e.g., due to source errors, non-availability of the source, transmission errors, non-reception, missing or erroneous alpha channel, data errors, other stream issues, etc.), which may result in the blended stream not displaying (or obscuring) the first live video stream (if the blended were displayed).

In some embodiments, the failover stream may be obtained from a failover buffer, which may be configured to store frames, lines, or portions thereof of the first live video input stream. For example, video from an endoscope may be stored in and then automatically and transparently obtained from a failover buffer when a blended stream contain invalid data are detected. Blending may be automatically resumed when the blended stream correctly incorporates the first live video stream. In some embodiments, the switching from blending to the failover buffer may occur within the time to process a single video image frame. In some embodiments, upon detection (prior to display) that the blended stream would not display or obscure the first live input video stream, display of the first input video input stream (e.g., from a failover buffer) may be initiated and the first live video stream may be displayed by one or more displays.

In conventional schemes, such unexpected failures may result in no image or a blank screen being shown to medical personnel. Because visualization of the first live video input stream is often central to the performance of many medical procedures, such failures are unacceptable and can detrimentally impact performance of the procedure causing delays, increasing the likelihood of errors, interrupting flow, and in some cases, could lead to the procedure being aborted. In addition, because such failures are unpredictable and can result in medical personnel suddenly "flying blind"—medical personnel may shun the use of normally productive equipment and tools. Thus, disclosed embodiments facilitate fault tolerant highly available continuous intraoperative visualization.

FIG. 1 shows an example diagram illustrating an example system for intraoperative visualization in accordance with certain embodiments disclosed herein. FIG. 1 shows patient 130 undergoing a medical procedure involving the use of an endoscope (not shown in FIG. 1) being operated by surgeon 120-2.

As shown in FIG. 1, apparatus 150 (hereinafter referred to as "hub 150") may receive data streams over network 170 (e.g., also referred to as hospital network 170), which may be coupled to devices that are local to the medical facility. Hub 150 may take the form of or include functionality of a computing device capable of graphics and video processing. Hub 150 may also receive multimedia streams such as a video stream from the endoscope (not shown in FIG. 1A) used by medical professional 120-2, pre-operative images (e.g., from storage or other devices coupled to network 170), and intra-operative images (e.g., from local imaging devices). Medical professional 120-2 may view the video from the endoscope using headmounted display (HMD) 140, which may display high-definition (HD) 3-dimensional (3D) or stereoscopic images. In some embodiments, video from the endoscope may be received by Hub 150, processed, and then transmitted wirelessly to HMD 140. In some embodiments, the endoscopic (first) input video stream seen by medical professional 120-2 may be blended with one or more second graphics streams such as graphics, AI input, sensor data, etc. based on the configuration of hub 150. Sensor data may include data from sensors associated with the endoscope or other instruments being used by medical professional 120, which may provide camera pose, instrument state, and other information. HMD 140 may be custom or a commercially available HMD.

In some embodiments, hub 150 may also receive AI information streams, including decision-support, video annotations (e.g., to mark blood vessels in images to prevent accidental cutting, to detect bleeding, etc.), warnings (e.g., based on current states of tissue and/or of endoscopic devices, etc.). The endoscope may be controlled using endoscopic controller 110, which may include and/or be coupled to display 115. In some embodiments, hub 150 may be capable of displaying an augmented view, which may comprise, for example, an endoscopic view augmented with one or more additional overlays, on display 115. As examples, the overlays may be simple (such as a toolkit for instrument use), or complex (such as a fusion of pre-operative images, which may be displayed in addition to toolkits, etc.)

In some embodiments, hub 150 may include or be coupled to an AI engine, which may perform some AI processing locally. In some embodiments, AI information streams may be received over network 170 and/or from cloud based services 180. Cloud based services may be hosted on private clouds, public clouds, and/or hybrid public-private clouds. AI functionality may be distributed between hub 150, computing devices, and other devices on hospital network 170, and cloud 180. For example, hub 150 may run models to provide AI based decision-support, video annotations etc., whereas AI related data may be de-identified (e.g., for patient privacy and regulatory reasons) and stored locally and/or on devices coupled to hospital network 170, while machine learning models may be trained and/or improved using the de-identified collected data using AI related applications provided on cloud 180.

In some embodiments, as shown in FIG. 1, example hub 150 may include a touchscreen display 165, which may be used to present user-interface (UI) to enable medical professional 120 to select input streams, select AI models to run, and configure other functionality such as display of endoscopic images, reception of sensor data, provide power to devices, and/or control instruments and/or devices coupled to hub 150. In some embodiments, touchscreen 165 may be detachable and capable of being wirelessly coupled to base unit 155 of hub 150. In some embodiments, touchscreen 165 may form part of a tablet computer and/or other mobile computing device and processing capability may be distributed between base unit 155 and the tablet or mobile computer that houses touchscreen 165. In some embodiments, base unit 155 may also serve as a docking station for touchscreen 165 and or other tablet computers and/or mobile computing devices.

In some embodiments, hub 150 may serve as a Wireless Access Point (WAP) and broadcast its own local network 160-1, which may be used by authorized devices (e.g., within the operating room and/or within range). Authorized devices may be connect to hub 150 (serving as a WAP) over network 160-1 and may be communicatively coupled to hub 150 over network 160-1. Hub centered network 160-1 may insulate various intraoperative devices in the operating room or in proximity to the operating room from wireless network outages, signal reception issues, bandwidth related issues, etc. that may occur in the wireless network provided by the hospital (e.g., hospital network 170) or medical facility. Thus, hub centered network 160-1 may facilitate increased bandwidth and lower latencies between intraoperative devices that are coupled to hub 150 and improve information sharing including video, images, graphics, and/or other information, while maintaining privacy. For example, hub 150 may receive images from an intraoperative imaging device (e.g., such as a fluoroscopic camera) in the operating room (OR) over network 160-1 and may display the image on display 135-1. As another example, hub 150 may send graphics and/or user-interface (UI) information for display on tablet computer 145. Medical professional 120-1 may use the UI remotely to configure hub 150 and/or one or more devices that are coupled to hub 150 over network 160-1.

Figure 2A:
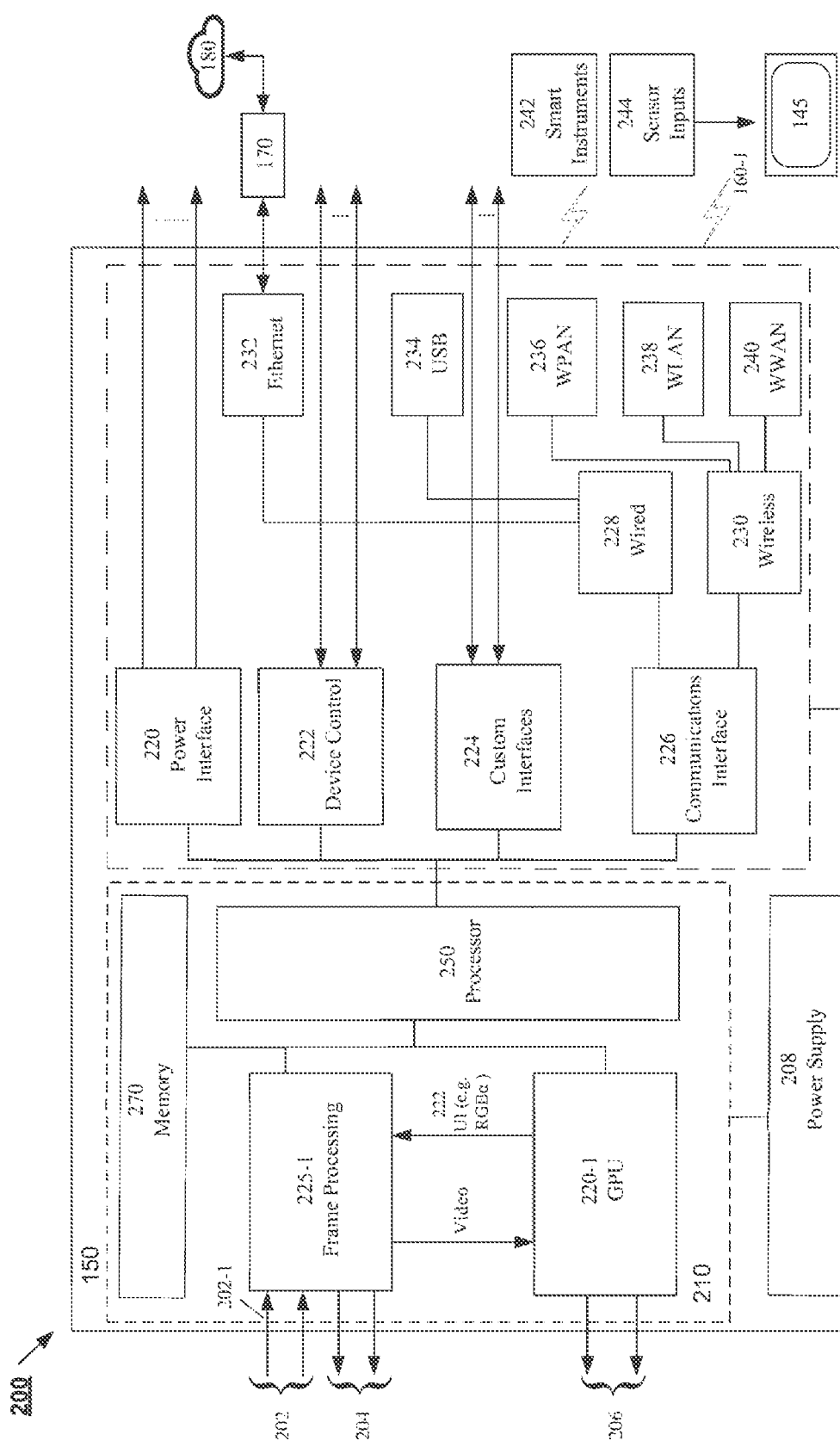
FIGS. 2A and 2B show schematic block diagrams of example embodiments of apparatus to facilitate fault-tolerant intraoperative visualization.
Figure 2B:
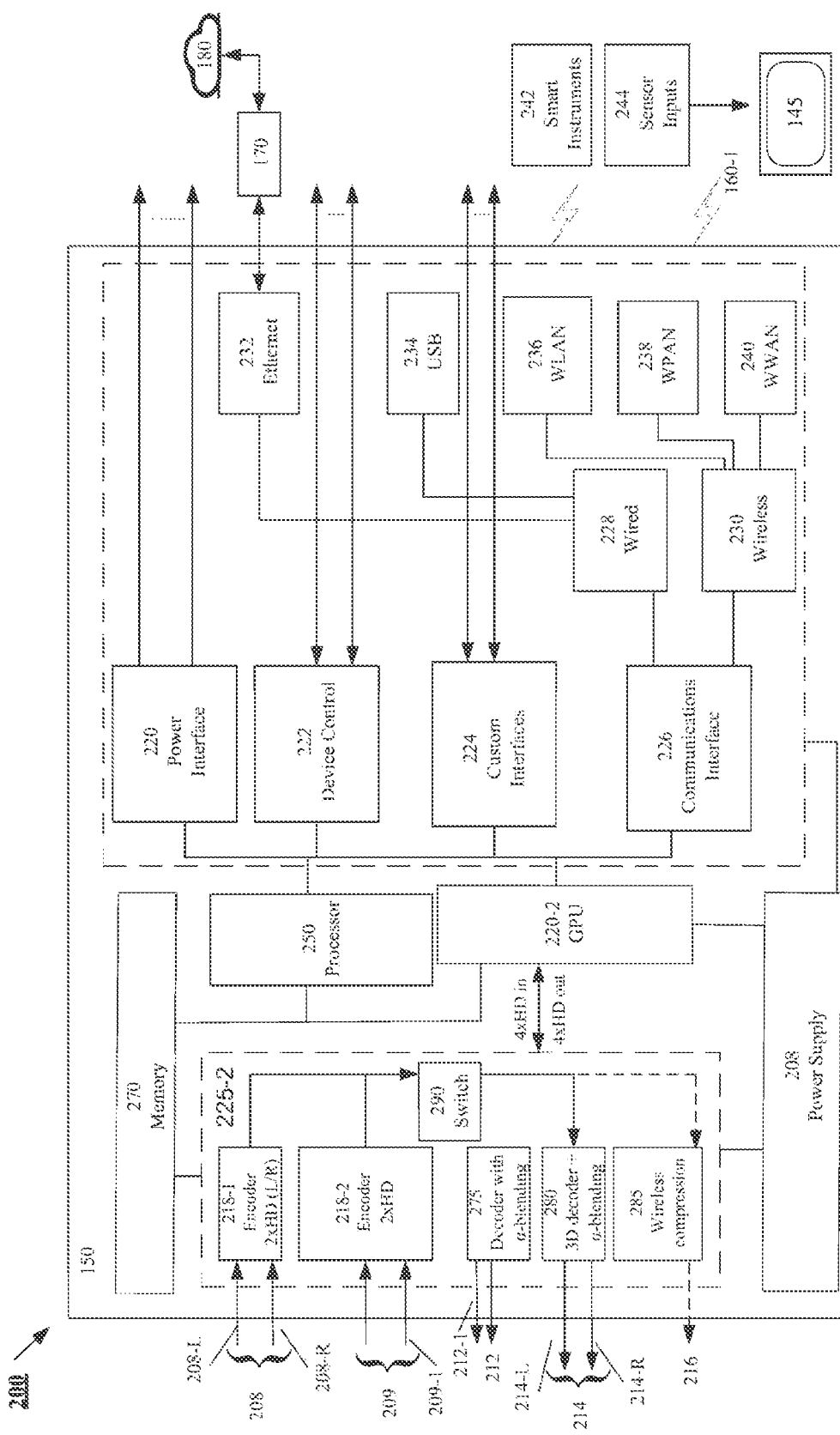

FIGS. 2A and 2B are schematic block diagrams 200 of an example system illustrating functional components of embodiments of an apparatus (such as example hub 150) that facilitates fault-tolerant intraoperative visualization.

As shown in FIG. 2A, frame processing engine (FPE) 255-1 in hub 150 may receive a plurality of input video streams 202 (e.g., High Definition (HD) video streams, for example, from an endoscope or ultrasound device). The input video streams 202 may include a first input video stream 202-1, which may correspond to a video stream associated with a procedure currently being performed by medical professional 120-1. The input video streams 202 may be provided over standard interfaces (e.g., such as High Definition Multimedia Interface (HDMI) or Serial Digital Interface (SDI), etc.) or custom interfaces. HD video may include 10-bit 4K video such as, for example, of resolution 3840×2160 pixels (which is also referred to as 2160*p*), 1920×1080 pixels (also referred to as 1080p video), and 1280×720 pixels (also referred to as 720p video) with a frame rate of 59.94 and/or 60 image frames per second (fps).

FPE 225-1 may also be capable of output of video streams 204. In some instances, the number of output channels may mirror the number of input channels and output video streams 204 may mirror the resolution and frame rate of the input video streams 202. Output video streams 204 may be transmitted over the HDMI and/or SDI interfaces. In some embodiments, output video streams 204 may also be transmitted wirelessly (e.g., over a Wireless Local Area Network (WLAN)) associated with hub 150. FPE 225-1 may include and/or be coupled to memory 270. Memory 270 may include a plurality of frame buffers (not shown in FIG. 2A), which may be used to store graphics frames and/or video frames. Graphics frames may be received with an "alpha" channel (e.g., as Red-Blue-Green-alpha or "RGBα"), which may indicate the degree of transparency associated with each pixel. The alpha channel may be separate or pre-multiplied. Graphics frames (e.g., UIs) may be received from Graphics Processing Unit (GPU) 220-1. In some embodiments, memory 270 may hold a plurality of frame buffers for each input video stream. In some embodiments, each frame buffer may be configured to be of the same size as the input video stream being processed. Video and graphics information in frame buffers associated with a channel may be blended based on the alpha information (e.g., in the graphics stream) and output by FPE 225-1.

In some embodiments, errors in the blended stream that would result in non-display or obscuring of the first live video stream 202-1 (e.g., from the endoscope used by medical professional 120-2) may be automatically detected, and a failover stream corresponding to the first live video input stream may be displayed to medical personnel. For example, one or more second input streams that are being blended may contain no data or invalid data (e.g., due to source errors, non-availability of the source, transmission errors, non-reception, missing or erroneous alpha channel, data errors, other stream issues, etc.), which may result in the blended stream not displaying (or obscuring) the first live video stream (if the blended were to be displayed).

In some embodiments, FPE 225-1 may automatically detect that the blended stream is faulty and, in response to fault detection, may output a failover stream (referred to herein as output stream "204-*f*") that corresponds to the first live video input stream 202-1. The detection of the faulty blended stream and the output of the failover stream 204-*f* may occur within the time to process and output a single frame, so that the transition is seamless. Output stream 204-*f* may include information to alert medical personnel 120 to the failure of the one or more second input streams. In some embodiments, the failover stream may be obtained from a failover frame buffer (hereinafter "failover buffer"), which may be configured to store frames, lines, or portions thereof of the first live video input stream. For example, first video input 202-1 from the endoscope may be stored in and then automatically and transparently obtained from a failover buffer when the one or more second input streams that contain invalid data are detected. In some embodiments, upon detection (prior to display) that the blended stream would not display the first live input video stream or would obscure the first live input video stream, then display of the first input video input stream (e.g., from a failover buffer) may be initiated and the first live video stream may be displayed by one or more displays. Further, blending may be automatically resumed when the blended stream correctly incorporates the live video stream and FPE 225-1 may then again output a blended video stream 204 (instead of failover stream 204-*f*).

In some embodiments, FPE 225-1 may be implemented using an Application Specific Integrated Circuit (ASIC), a Field Programmable Gate Array (FPGA) add-on board, and/or using some combination of hardware, software, and firmware. As one example, FPE 225-1 may use FPGAs in an M2 form factor and use the Peripheral Component Express (PCIe) interface to communicate with GPU 220-1 processor 250 and/or other components on hub 150. PCIe is a high-speed serial computer expansion bus standard. In the embodiment above, FPE 225-1 may be added as a solution to an existing computing platform such as a PC. For example, FPE 225-1 (e.g., as an add-on PCIe component) may be used to add functionality disclosed herein to an existing computing platform that may lack features disclosed herein. In some embodiments, FPE 225-1 and other hub components may receive power from Power Supply 208, which may be compliant with the IEC 60601-1 standard for medical equipment. IEC 60601-1 is a series of standards related to the basic safety and essential performance requirements of medical electrical equipment.

GPU 220-1 may perform graphics and AI processing. For example, GPU 220-1 may include Tensor Processing Units (TPUs) or tensor cores, which may be capable of running AI models, graphics processing including 3D graphics, video rendering, etc. GPU 220-1 may be able to receive and process video input from FPE 225-1 and pre-operative and intra-operative images related to patient 130. AI applications running on GPU 220-1 may process the received input to determine and mark blood vessels, bleeding, etc. in frames. In some embodiments, GPU 220-2 may provide graphics and/or UIs and/or augmentations in real-time to FPE 225-1, which may be provided to medical professionals 120 intra-operatively as decision support, guidance, warnings, etc. using annotations/augmentations to video. GPU 220-1 may also receive video input from FPE 225-1, which may be displayed along with any augmentations on displays 135-1, 165 (FIG. 1) and/or on tablet 145.

Although shown as separate from FPE 225-1, functionality associated with one or more of GPU 220-1, processor 250 and memory 270 may be combined with FPE 225-1 (e.g., as single component, chip, or card), or be external to FPE 225-1. For example, memory 270 may be distributed across hub 150 so that one or more components such as processor 250, FPE 225-1, and/or GPU 220-1 may each include local memory and may also access a main or system memory. Further, memory 270 may include primary and/or secondary memory.

Program code, data, images, configuration information, graphics, image and video frames, models—including AI models, etc. may be stored in memory 270, and read and/or executed by one or more of FPE 225-1, GPU 220-1, and/or processor 250 to perform the techniques disclosed herein. As used herein, the term "memory" refers to any type of long term, short term, volatile, nonvolatile, or other memory and is not to be limited to any particular type of memory or number of memories, or type of media upon which memory is stored. Examples of storage media include computer-readable media encoded with databases, data structures, etc. and computer-readable media encoded with computer programs. Computer-readable media may include physical computer storage media. A storage medium may be any available medium that can be accessed by a computer. By way of example, and not limitation, such computer-readable media can comprise Random Access Memory (RAM) and variations thereof including Non-Volatile RAM (NVRAM), Read Only Memory (ROM) and variations thereof Erasable Programmable (EPROM), Flash Memory, etc. Computer-readable media may also include Compact Disc ROM (CD-ROM), memory cards, portable drives, or other optical disk storage, magnetic disk storage, solid state drives, other storage devices, or any other medium that can be used to store desired program code in the form of instructions and/or data structures and that can be accessed by a computer; disk and disc, as used herein, includes compact disc (CD), laser disc, optical disc, digital versatile disc (DVD), floppy disk and Blu-ray disc where disks usually reproduce data magnetically, while discs reproduce data optically with lasers. Combinations of the above should also be included within the scope of computer-readable media.

Communications interface 226 may be capable of wired (e.g., using wired communications interface 228) or wireless (e.g., using wireless communication interface 230) communications with another device (e.g., HMD 140) and may be used to receive sensor inputs 224, communicate with smart instruments 242, and/or external networks such as hospital network 170 (FIG. 1)).

Captured images, AI models, instrument state, sensor input 242, input from smart instruments 244, robot data, etc., may be received over communications interface 226. User input (e.g., received from tablet 145) may also be received and confirmations/messages transmitted using communications interface 226. Wireless communication may include communication using one or more of: Wireless Local Area Network (WLAN) interface 238 (e.g., with tablet 145, display 140, over Wi-Fi etc.), which may be based on the IEEE 802.11 standards, and/or over Wireless Wide Area Networks (WWAN) interface 240 (e.g., with a remote mobile device, cloud based edge server over cloud 180, etc.), which may be based on cellular communication standards such as a Fifth Generation (5G) network, or Long Term Evolution (LTE), and/or over Wireless Personal Area Networks (WPAN) interface 236 (e.g., with audio devices, some proximate smart instruments 242, etc.), which may be based on IEEE 802.11x (e.g., using Bluetooth, etc.).

In some embodiments, cloud based applications, AI models, pre-operative and intra-operative images, etc. may be downloaded by processor using wired interface 228 from one or more devices coupled to hub 150 over USB interface 234, and/or servers coupled to hospital network 170 over Ethernet 232, and/or from cloud based servers coupled to cloud 180 over Ethernet 232.

In some embodiments, processor may also send commands to control devices based on input received from a medical professional 120, or based on instrument state, sensor input, configuration settings, etc. using device control interface 222 or over communications interface 226. Power interface 220 may be enabled by processor 150 to supply power to one or more instruments, sensors, and/or other devices coupled to hub 150. Hub 150 may receive power from power supply 208, when plugged in and, in some embodiments, may include backup battery power.

Processor 150 may also communicate with devices (e.g., robotic or other devices) over custom interfaces 224, which may be proprietary. In some embodiments, processor may also run program code to control operation of hub 150, log events, notify medical personnel (e.g., via messages), store data, images, sensor input, pull up patient records from databases (local or networked), facilitate maintenance of synchronization for multi-media operations, provide support for the Digital Imaging and Communications in Medicine (DICOM) and other standards, facilitate access to cloud based services etc. For example, based on user input and configuration information, processor 150 may log and record a procedure performed using an endoscope for replay (e.g., for training and/or review) and/or analysis (e.g., to train a machine learning/AI model) at a subsequent time. As another example, processor 150 may facilitate the live streaming of the procedure via communications interface 226 (e.g., for educational or training purposes). DICOM is a standard for communication and management of medical imaging information and related data between devices.

The methodologies described herein may be implemented in hardware, firmware, software, or any combination thereof. For a hardware implementation, processor 250, FPE 225, GPU 220 may be implemented within one or more application specific integrated circuits (ASICs), digital signal processors (DSPs), image processors, digital signal processing devices (DSPDs), programmable logic devices (PLDs), field programmable gate arrays (FPGAs), processors, controllers, micro-controllers, microprocessors, electronic devices, other electronic units designed to perform the functions described herein, or any combination thereof. Processor 250 and GPU 220 may also include functionality perform other well-known computer vision and image processing functions such as feature extraction from images, image comparison, image matching, object recognition and tracking, image compression and decompression, mixing—including line-wise mixing, alpha blending, etc. The components and/or blocks shown in FIGS. 2A and 2B (e.g., processor 250, GPU 225, FPE 220, memory 270, communications interface 226, etc.) may be coupled using buses, interfaces (e.g., PCIe, etc.), wired connections, etc.

FIG. 2B is a schematic block diagram 200 of an example system illustrating functional components of another embodiment of an apparatus (such as example hub 150) that facilitates intraoperative visualization. Components with similar labels function in a manner similar to that described in FIG. 2A. The description of FIG. 2B describes an embodiment reflecting some changes in function, behavior, or interaction of functional blocks and/or components relative to FIG. 2A.

As shown in FIG. 2B, encoder 218-1 may receive and encode 3D HD video stream 208 (e.g., from a 3D or stereoscopic camera associated with endoscope), which may include a left video channel 208-L and a right video channel 208-R each at 60 fps. Further, as shown in FIG. 2B, encoder 218-2 may receive and encode 2 separate HD streams 209 (e.g., from a C-arm extension camera and an ultrasound device) each at 60 fps. Switch 290 may receive encoded input video streams 208 and 209 as well as graphics input from GPU 220-2 in the form of RGBα streams (an RGB stream with an α channel). As shown in FIG. 2B, switch 290 may be capable of sending 4 HD input streams each at 60 fps and receiving 4 HD graphics RGBα streams each at 60 fps to/from GPU 220-2. Switch 290 may be configured to send encoded input stream 208 and RGBα stream to 3D decoder with alpha blending 280. Similarly, switch 290 may be configured to send encoded input streams 209 and RGBα stream to decoder with alpha blending 275 and/or to compression and wireless transmission block 285.

In normal operation, for example, when a blended (graphics and video) frame output by 3D decoder with alpha blending 280 frame correctly incorporates input video channels 208, the blended streams may output as 3D video stream 214 (e.g. to HMD 140), which may include a left video channel 214-L and a right video channel 214-R each at 60 fps. As another example, when a blended (graphics and video) decoder output by decoder with alpha blending 275 frame correctly incorporates input video channels 209, the blended streams may output as HD streams 212 each at 60 fps.

In instances when the blended stream is faulty and fails to correctly incorporate input video streams 208 and/or 209, then, FPE 225-2 may automatically detect the faulty blended stream and, in response to detection of the faulty blended stream, may output a failover stream (referred to herein as output stream "214-$f$" or 212-$f$" that corresponds to the first live video input stream 208 or 209, respectively).

The faulty blended stream may result from one or more of the second input graphics RGBα streams containing no alpha data or invalid alpha data (e.g., due to source errors, non-availability of the source, transmission errors, non-reception, alpha channel error, data errors, other stream issues, etc.). In the situation described above, the faulty blended stream would result in a black screen and/or in the live input video streams (208 or 209) not being displayed—if the blended stream were output and displayed. In the situation described above, FPE 225-2 may automatically detect the faulty blended output stream and, may output a failover stream (referred to herein as output stream "214-$f$" or 212-$f$" that corresponds to the first live video input stream 208 or 209, respectively). The detection of erroneous second input stream and output of the failover stream may occur within the time to process and output a single frame, so that the transition is seamless. Output streams 214-$f$ or 212-$f$ may include information to alert medical personnel 120 to the failure of the one or more second input streams.

In some embodiments, the failover stream may be obtained from a failover buffer, which may be configured to store frames, lines, or portions thereof of the first live video input stream. A failover buffer may be accessible to each of decoder with alpha blending 275 and 3D decoder with alpha blending 280. For example, first video input 208 from the endoscope may be stored in and then automatically and transparently obtained from a failover buffer when the one or more second input streams that contain invalid data are detected. Further, blending may be automatically resumed when the one or more second input streams include valid data and FPE 225-2 may then again output a blended video stream 214 (instead of failover stream 214-$f$).

As shown in FIG. 2B, FPE 225-2 may also include wireless compression block 285, which may compress one or more of the input streams for wireless transmission. In FIG. 2B, for simplicity, stream 216 is shown as being output by wireless compression block 285. However, stream 216 may be sent to communication interface 226 by wireless compression block 285, and then output using wireless communication interface 230 and/or WLAN interface 236.

Figure 3:
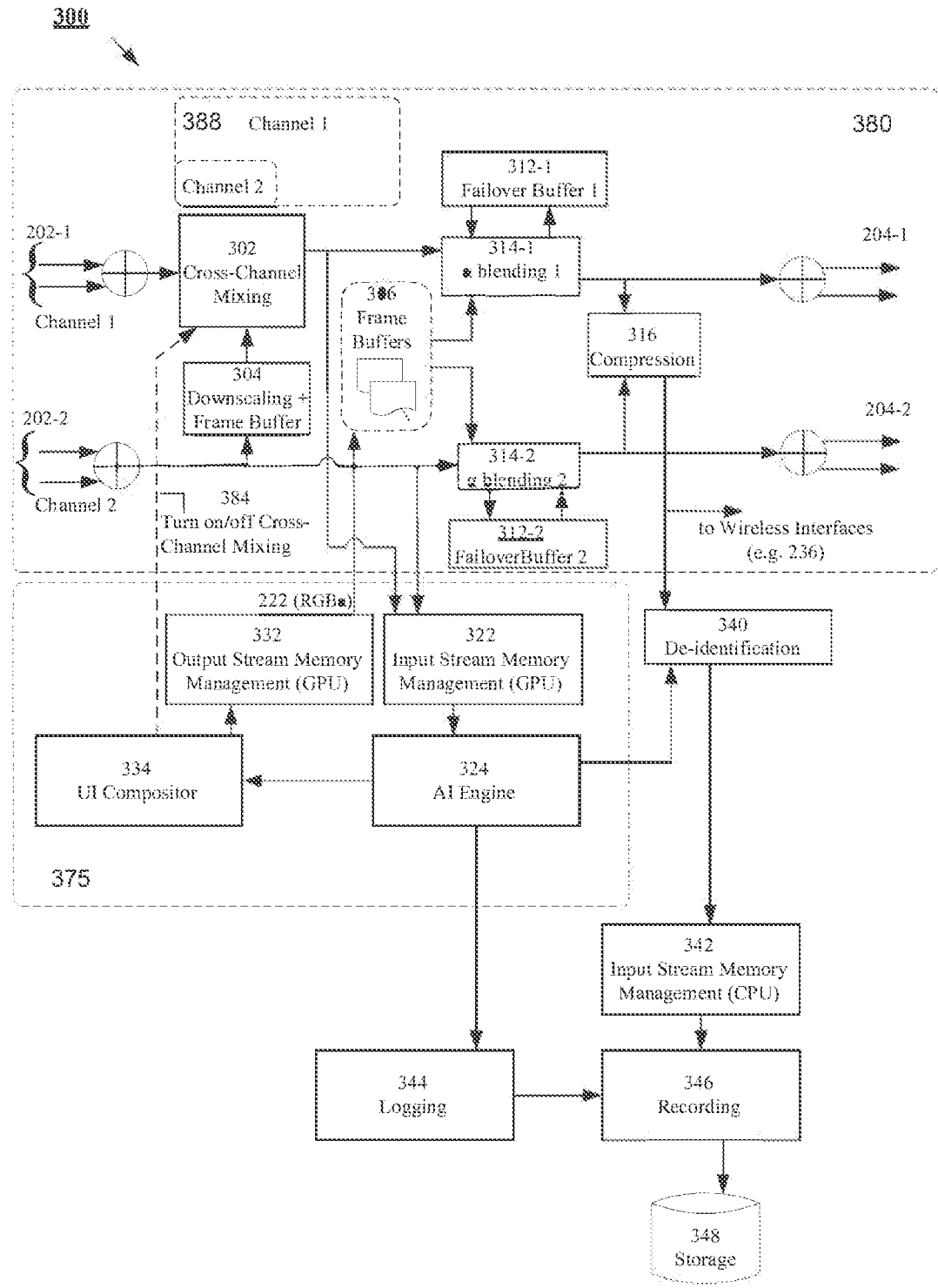
FIG. 3 shows an example diagram showing signal flow between functional blocks of an apparatus to facilitate fault-tolerant intraoperative visualization.

FIG. 3 shows a schematic block diagram 300 illustrating signal and data flow between functional blocks of an apparatus to facilitate intraoperative visualization such as hub 150. In some embodiments, blocks 375 and 380 (shown by dashed lines in FIG. 3) may form part of FPE 225 and GPU 220, respectively.

As shown in FIG. 3, in some embodiments, cross channel mixing block 302 may receive first input video stream 202-1 and obtain an appropriately downscaled version of second input video stream 202-2 (e.g., from downscaling+frame buffer 304) and may mix the two channels to obtain example mixed frame 388. In some instances, first input video stream and second input video stream may be the left and right channels of a 3D HD video stream (e.g., such video stream 208 in FIG. 2B). In other instances, first input video stream and second input video stream may be independent video streams received from two different devices (e.g., such as an endoscope and an ultrasound device).

In some embodiments, as shown in FIG. 3, each input stream (e.g., 202-1) may be received either over an HDMI and/or SDI interface and the appropriate interface may be selected for input. In some embodiments, second input video stream 202-2 may be downscaled based on mixing parameters and placed in an appropriately sized frame buffer by downscaling and frame buffer block 304, prior to being input cross channel mixing block 302. Example mixed frame 388 is shown merely to illustrate a mixed frame. In practice, the appearance of the mixed frame may depend on cross channel mixing parameters. Cross-channel mixing may be performed when cross-channel mixing is turned on by cross channel mixing enable signal 384.

In some embodiments, time stamps associated with the streams 202-1 and 202-2 and other input streams may be synchronized. In some embodiments, the timestamps associated with the input streams may be synchronized using Network Time Protocol (NTP), or Simple Network Time Protocol (SNTP), or by other appropriate methods.

Cross-channel mixing performed by cross-channel mixing block 302 may be turned on or off by cross-channel mixing enable signal 384 from UI compositor block. In instances, where cross-channel mixing is turned off, no cross-channel mixing will be performed by cross-channel performed by cross-channel mixing block 302. In some embodiments, the output of cross-channel mixing block 302 (e.g., first input video stream 202-1 when cross-channel mixing is turned off or the mixed stream when cross-channel mixing is on) and second input video stream 202-2 may also be received by: (a) input stream memory management block 322, which may form part of GPU 220, and (b) alpha-blending block 314-1 (which receives the output of cross-channel mixing block 302) and alpha-blending block 314-2 (which receives second input video stream 202-2). In some embodiments, the RGBα stream 222 output by output stream memory management block 332 may be stored in frame buffers 306. In some embodiments, each stream may have at least two frame buffers, one being written while another is read/processed and logic may switch between the two buffers. In some embodiments, the input video streams 202 may be blended (e.g., by alpha-blending blocks 314) with the RGBα stream 222.

In some embodiments, the output of cross-channel mixing block 302 and second input video stream 202-2 may be forwarded by input stream memory management block 322 to AI Engine 324, which may de-identify the input data in accordance with patient privacy and other data regulations and then run AI models on the input streams to provide decision support, identify features (e.g., blood vessels, bleeding, etc.), make augmentations, provide warnings and/or suggestions, etc. in real-time. The output of AI engine 324 may be provided to User-Interface (UI) compositor block 334, which may composite the input of AI engine 324 with other UI elements and send the composited UI stream to output stream memory management block 332, which may output and store RGBα stream 222 (corresponding to the composited UI stream) in frame buffers 306. The output of AI engine 324 may be logged by logging block 344 and may also be provided to de-identification block 340, where further de-identification (if appropriate) may occur. De-identification block 340 may provide the de-identified stream along with output video streams to input stream memory management block 342 (e.g., which may run on or be associated CPU 250), which may use recording block 346 to record and store the streams in storage 348 along with any logging information provided by logging block 344.

In some embodiments, alpha-blending block 314-1 (which receives the output of cross-channel mixing block 302) and alpha-blending block 314-2 (which receives second input video stream 202-2) may also store the received input streams (e.g., 202) in failover buffers 312-1 and 312-2, respectively.

In normal operation, when valid graphics data (with a valid alpha channel) is obtained by alpha-blending block 314-1 and alpha-blending block 314-2 from corresponding frame buffers 306, then the blended stream output will correctly include the live input video streams (e.g., output of cross-channel mixing block 302 and second input video stream 202-2) and output as streams 204-1 and 204-2, respectively. In instances where first input video stream and second input video stream may be the left 208-L and right 208-R channels of a 3D HD video stream (e.g., such as video stream 208 in FIG. 2B) and the output may reflect the input streams in the left 214-L and right 214-R channels of blended output 3D HD video stream 214 (in FIG. 2B) or the left 204-L and right 214-R channels of blended output 3D HD video stream 204 (in FIG. 3). In some embodiments, the streams may be output to HMD 140.

In instances, when the blended stream is faulty and does not correctly incorporate the input live video streams (e.g., output of cross-channel mixing block 302 and second input video stream 202-2), then alpha-blending block 314-1 and alpha-blending block 314-2 may: (i) automatically detect that the blended stream contains errors and (ii) may each output a failover stream (e.g., output stream "204-1f" or 204-2f" that correspond to the output of cross-channel mixing block 302 and second input stream 202-2, respectively). As one example, the blended stream may be faulty when one or more of the input graphics RGBα streams 222 that are being blended contain no data or invalid data and/or are missing alpha information (e.g., due to source errors, non-availability of the source, transmission errors, non-reception, missing or bad alpha channel, data errors, other stream issues, etc.). When the faulty graphics RGBα streams 222 are blended, the blended output (if displayed) could result in a black screen and/or the non-display or obscuring of the input live video stream (e.g., non-display or obscuring of the output of cross-channel mixing block 302 and second input video stream 202-2). In some embodiments, the detection of the faulty blended stream and output of the failover streams 204-1f and 204-2f may occur within the time to process and output a single frame, so that the transition is seamless. Output streams 204-1f and 204-2f may include information to alert medical personnel 120 to errors in RGBα streams 222.

In some embodiments, the failover streams 204-1f and 204-2f may be obtained from failover buffers 312-1 and 312-2, respectively, which may be configured to store frames, lines, or portions thereof of the output of cross-channel mixing block 302 and second input stream 202-2, respectively. Blending may be automatically resumed when the blended stream includes valid data and alpha-blending block 314-1 and alpha-blending block 314-2 may then again output a blended video stream 204 or 214 (instead of failover streams 204-f or 214-f). The output streams 204-1 and 204-2 may also be received by compression block 316, where they may be compressed for wireless transmission (e.g., over WLAN interface 236).

Figure 4:
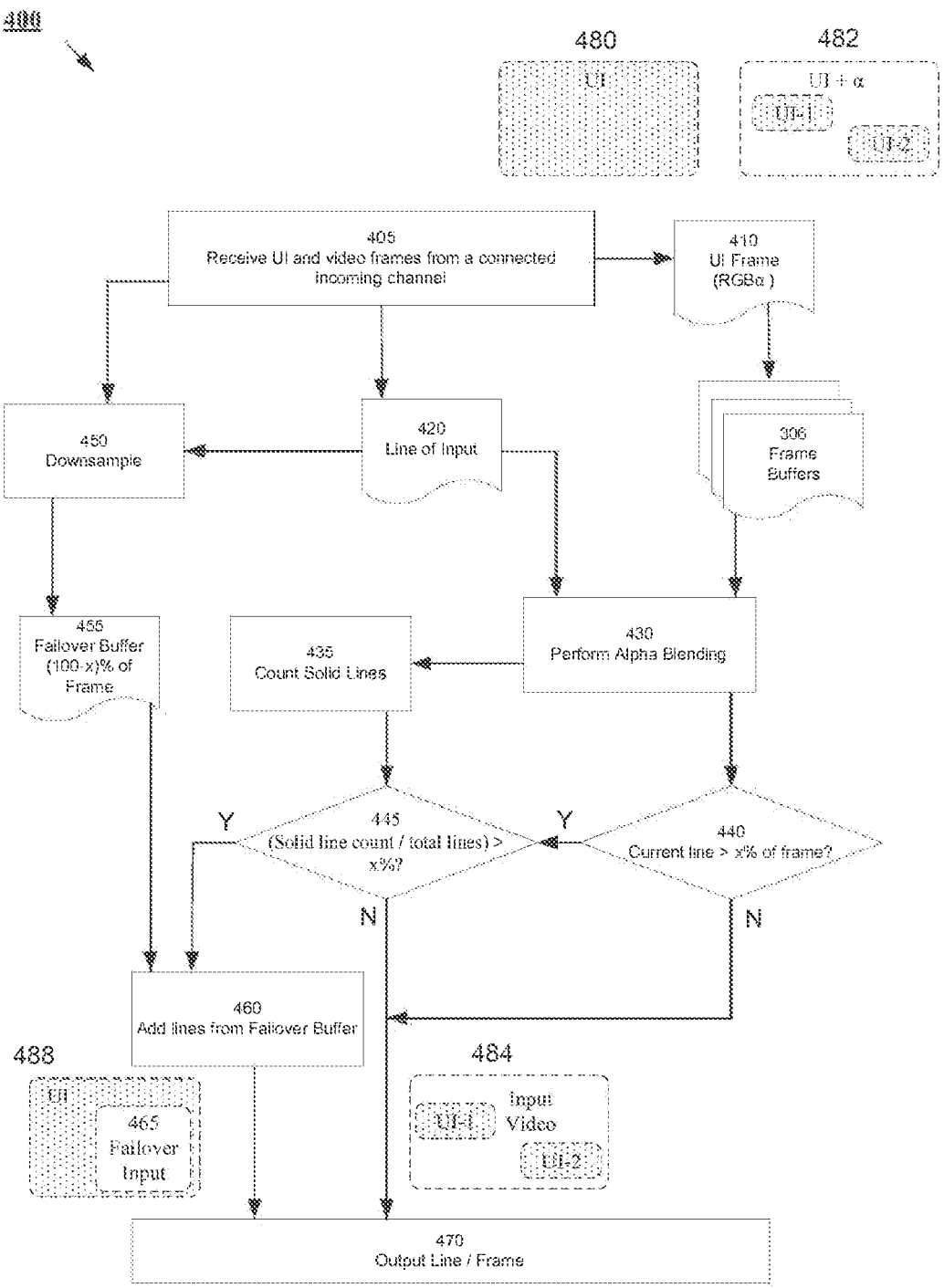
FIG. 4 shows a flowchart of an example method to facilitate fault-tolerant intraoperative visualization with failover functionality

FIG. 4 shows a flowchart of an example method 400 to facilitate intraoperative visualization with failover functionality. In some embodiments, some or all of method 400 may be performed by hub 150, and/or functional elements of hub 150 such as FPE 225 and/or alpha blending blocks 314 (FIG. 3), and/or decoder with alpha blending blocks 275 and/or 3D decoder with alpha blending block 280 (FIG. 2B). Method 400 may be iteratively performed for each incoming frame.

In block 405, a graphics/UI frame (e.g., a frame from RGBα stream 222) and a first video frame (e.g., first video frame 202-1) may be received from a connected incoming channel. As shown in FIG. 4, the graphics/UI frame may either: (a) include an alpha channel as indicated by example UI (RGBα) frame 482, or (b) be erroneous, as in example UI frame 480, where the alpha channel is missing. In some embodiments, the received video frame and UI frame may be stored frame buffers 306. For example, UI frame 410, which is shown in FIG. 4 as including an alpha channel may be stored in frame buffers 306.

In block 430, alpha blending may be performed using the first or next line 420 of first input video channel (e.g., 202-1) and a corresponding line in UI frame 410 stored in frame buffers 306. In some embodiments, perform alpha blending block 430 may detect each solid (e.g., black) line in the current frame and send an indication to count solid lines block 435.

In some embodiments, count solid lines block 435 may maintain a running count of solid UI frame lines (e.g., solid lines in UI frame 410) and may increment the number of solid lines each time it receives an indication of detection of a solid line from perform alpha blending block 430.

In block 440, if the current line number is not greater than some fraction x of the frame (e.g., less than x % of the frame has been processed), then the blended frame may be maintained as the output, which, when UI frame 410 is valid and includes a correct alpha channel, may appear, upon completion, as example blended frame 484.

In block 445, if the solid line count divided by total number of lines in the frame exceeds x % (e.g., solid lines make up more than x % of the frame) ("Y" in block 445), then block 460 may be invoked. In block 445, if the solid line count divided by total number of lines in the frame does not exceed x % (e.g., solid lines make up less than x % of the frame) ("N" in block 445), then the blended frame continues to be output, which, when UI frame 410 is valid and includes a correct alpha channel, may appear, upon completion, as example blended frame 484.

In block 450, each line of input may be downsampled (e.g., based on the dimensions of failover buffer 455) and stored in failover buffer 455. In some embodiments, failover buffer may be (100–x) % of the frame. As one example, x % may be selected as 66.67% and form $\frac{2}{3}^{rd}$ of the frame, while the failover buffer dimensions may form 33.33% or $\frac{1}{3}^{rd}$ of the frame. The downsampling may occur in real time.

In block 460 (which is invoked when solid lines make up more than x % of the total line count of the frame), the failover buffer is used as shown in example output frame 488, which includes failover input 465.

In block 470, the appropriate frame is output. The output frame may be one of frame 488 (e.g., if the UI frame is determined to have line errors that make up more than x % of the total line count of the frame) or frame 484 (e.g., when UI frame is determined to be valid and line errors do not make up more than x % of the total line count of the frame).

Figure 5A:
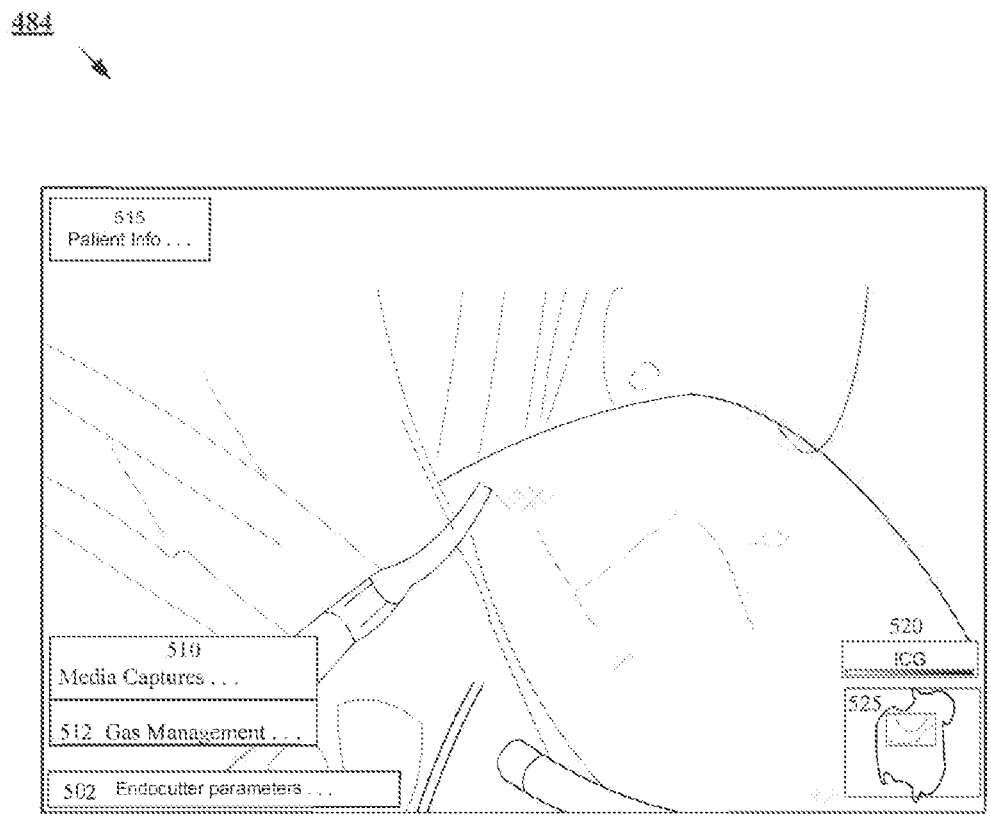
FIGS. 5A and 5B show example images illustrating operation of a system to facilitate fault-tolerant intraoperative visualization.
Figure 5B:
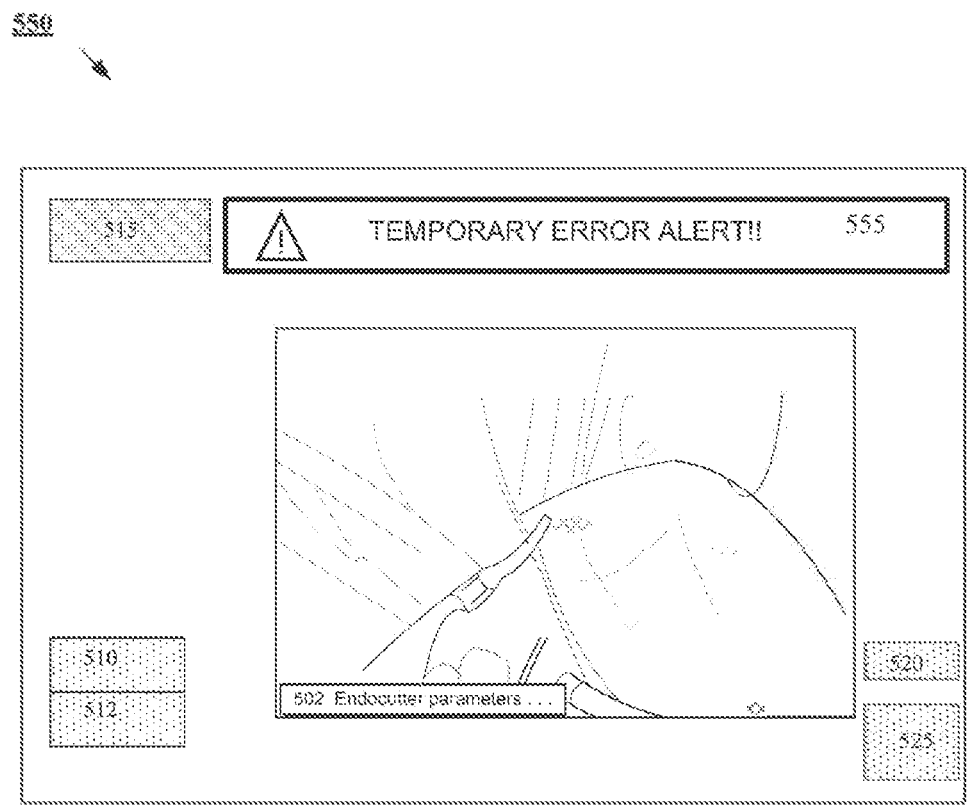

FIGS. 5A and 5B show example images illustrating operation of a system to facilitate intraoperative visualization.

FIG. 5A shows an example (correct) blended frame 484 with first video input from an endoscope (e.g., video frame 202-1) showing endoscopic tools such as endoscopic cutter along with current endocutter parameters. Blended frame 500 includes UI input (e.g., which may be provided as RGBα frame 222 by GPU 220 using UI compositor 334 via output stream memory management block 332). UI input may include one or more sub-windows such as: example patient info sub-window 515, which may provide information about patient 130 (e.g., retrieved by hub 150 from a server coupled to hospital network 170); media captures sub-window 510, which may provide information about the number of available video streams and image streams; gas management sub-window, which may provide information pertaining to parameters such as insufflation pressure, air flow, etc.; map 525, which provides a higher level indication of the location of the intraoperative procedure within the human body and/or within a portion of the larger anatomy/organ; and Indocyanine Green (ICG) display sub-window, which may allow changing of display modes of a fluoroscopic image; etc.

FIG. 5B shows the output frame when the bended frame is faulty. For example, the input UI frame 488 may be invalid or erroneous (e.g., because of the absence of alpha channel information or an excess of solid lines relative to the total number of lines in the UI frame), accordingly when blended frame 550 is displayed sub-windows 510, 512, 515, 520, and 525 do not contain information. However, first video input frame (e.g., 202-1) that is part of blended frame 550 continues to be displayed using information from the failover buffer (e.g., 312-1 or 455), thus facilitating continued visualization of the intraoperative procedure. Further, the medical professional (e.g., medical professional 120-2) is alerted to the temporary failure via the error message displayed in sub-window 555. In some embodiments, error message sub-window 555 may be placed in in an area not being used to display the first video frame. In some embodiments, the switch from blended frame 500 to blended frame 550 may be seamless and occur in a time less than that to process and output a single blended frame.

Figure 6:
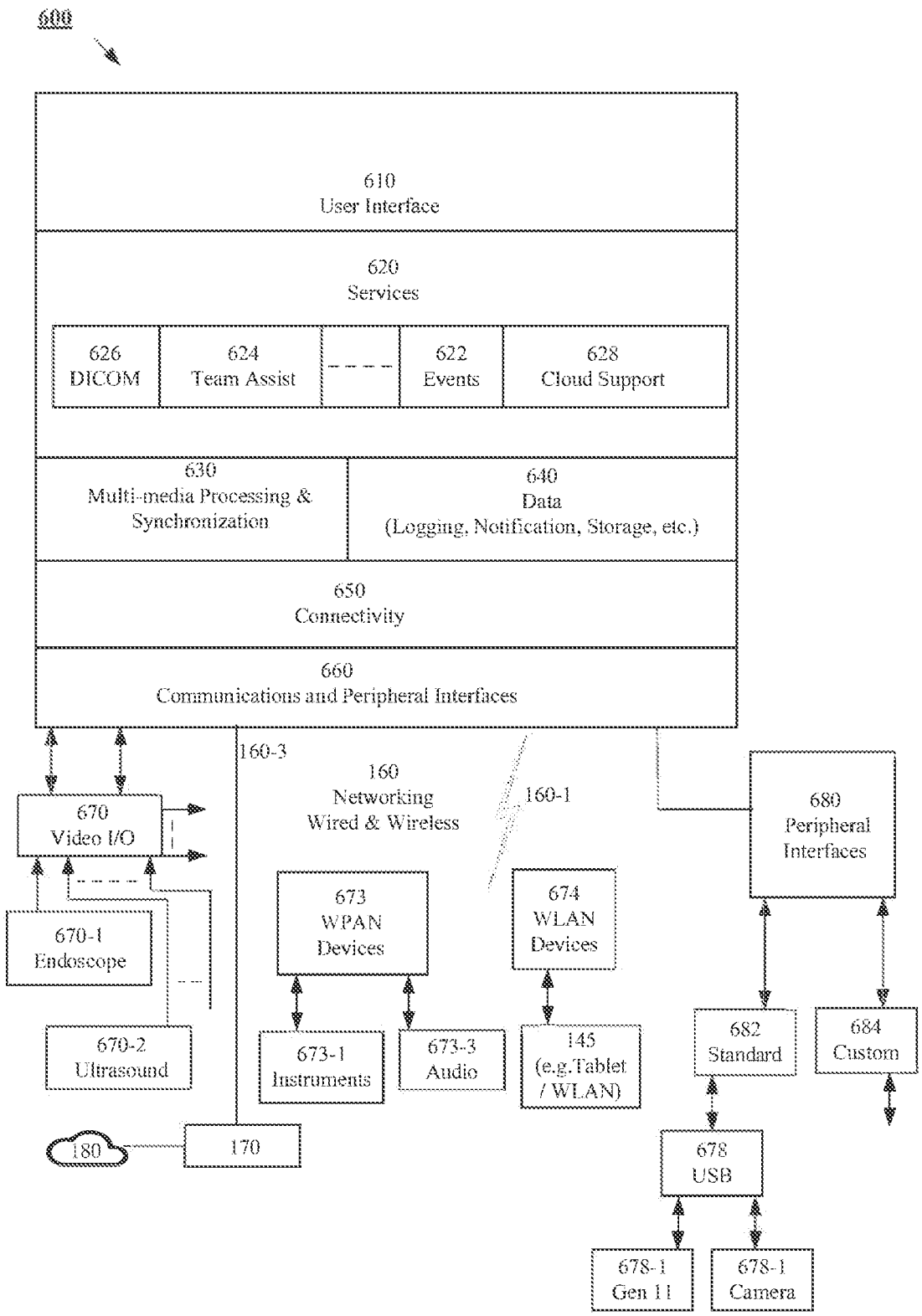
FIG. 6 shows an example software architecture associated with a system for intraoperative visualization in accordance with certain embodiments disclosed herein.

FIG. 6 shows an example system 600 illustrating the associated software architecture to support intraoperative visualization in accordance with certain embodiments disclosed herein. In some embodiments, some or all of the software architecture shown in FIG. 6 may be implemented on hub 150.

As shown in FIG. 6, software architecture 600 may include communication and peripheral services layer 660 (to support interfacing & communication with external devices), connectivity layer 650 (to enable capture of incoming information and format and package information for output via communication and peripheral services layer 660), data layer (to enable intraoperative event logging, event notification, and data management including data storage and upload to online web-based portals), multimedia processing and synchronization layer UI layer 610, which may allow users to authorize connection of one or more devices, configure coupled devices, select streams, select AI models to run, select pre-operative and intra-operative image sources, configure procedure guidance (e.g., to be provided to medical professionals 120 and/or support staff), specify notifications (e.g., to be provided to personnel upon the occurrence of certain events), configure telementoring, etc.

Services layer 620, which may be modular, may provide capability to enable advanced applications including AI based applications to be used in an intraoperative setting. For example, services layer 620 may provide: (a) DICOM services functionality 626, which may catalog and list available sources for relevant preoperative images and may retrieve and store selected images locally.

Services layer 620 may also provide (b) team assist services functionality, which may catalog and list available AI models for selection and running on live input video streams (e.g., to identify and mark blood vessels, etc.); (c) event services functionality 622, which may record and log events; (d) cloud support services, which may allow access to cloud based applications, models, data service providers, etc. and also allow uploading of data for training AI models, etc. Services layer 620 may also provide various other functionality such as a UI services functionality, which may allow interaction between UI layer and services.

In some embodiments, team assist services 624 may facilitate staff guidance to set up procedure guides for specific procedures preoperatively and then use these guides intraoperatively to follow steps outlined in the guide. Machine Learning models may be trained offline based on recorded video and procedure setup for specific procedures to automatically recognize phases and steps outlined as part of the procedure. In some embodiments, the trained models may then process live endoscope video feed in real time to automatically recognize steps and phases and auto-advance an on-screen guide to the next step in a procedure guide by changing content.

Team assist services 624 may further include notification related services to facilitate messaging from within the operating room (OR) to personnel outside the OR based on the current status of a procedure. Messages may include one or more notifications such as: a procedure has started, a procedure is likely to complete or go past the scheduled time, an OR is ready, etc. Such notifications may help with planning and more effective use of resources.

In some embodiments, team assist services 624 may include image viewing and image based planning functionality, which may facilitate processing, review, analysis, communication, and media interchange of multi-dimensional digital images acquired pre-operatively (e.g., from Computed Tomography (CT), Magnetic Resonance Imaging (MRI), Diagnostic Ultrasound, X-Ray, Positron Emission Tomography (PET) scans etc.) from imaging devices. Image viewer and image based planning may also facilitate preoperative surgical planning, and the intraoperative display of digital images by enabling 3D rendering and visualization and picture archiving and communication system (PACS) integration. In some embodiments, image viewing and image based planning functionality may also make the above information available over a network or over the web to authorized personnel and facilitate deployment of an online Digital Surgical Portal.

Integrated anatomy, 3D modeling, & patient outcome simulation functionality provided by team assist services 624 may use available pre-operative and intraoperative 3D models and facilitate display and manipulation of the 3D models for pre-operative planning and intra-operative reference and may improve visualization of anatomy and tumors and facilitate performance of patient-specific and procedure-specific simulation.

Multimedia processing and synchronization layer 630 may facilitate management and synchronization of connected input devices, enable data, video, and audio fusion and processing, and also provide services for data management (storage, retrieval, labeling, indexing, etc.)

Data layer 640 may facilitate scalable multi-service and device communication, provide notifications to all stakeholders related to intraoperative workflow, and facilitate systematic logging and storage of intraoperative information over hospital network 170 and/or through a cloud based data service provider.

Connectivity layer 650 may include functionality to facilitate multimedia data exchange and capture multimedia input received in various formats and over a variety of hardware interfaces such as video, audio, custom interfaces, and may also output information to connected displays as well as to tablet 145.

Communication and peripheral interface layer 660 may include software to configure and manage WLAN (e.g., Wi-Fi), WPAN (e.g., Bluetooth), WWAN (e.g., 5G), Ethernet, USB, custom peripheral port connectivity, etc.

As shown in FIG. 6, Communication and peripheral interface layer 660 may facilitate interaction with a variety of external devices and peripherals. For example, video inputs and outputs 670 may use the HDMI and/or SDI interfaces to receive video from devices such as endoscope 670-1, ultrasound 670-2, etc. Video inputs and outputs 670 may also output video to external displays 135 (not shown in FIG. 6).

Wired and wireless networking interface 160 may include wired network connections such as Ethernet connection 160-3, which may be used to: connect to servers, storage, services etc. on hospital network 170; facilitate data exchange with the digital surgical portal; and may provide connectivity to cloud based storage and/or services 180. Wireless network 160-1 may include interfaces for WLAN connections with external WLAN devices 174 such as tablet 145, which may allow users to interact with, configure, and manage system 600. In some embodiments, a local (e.g., operating room) wireless network 160 may be provided by hub 150, which may be used by authorized devices with access to the network to communicate with hub 150 and/or among themselves (e.g., improving bandwidth, latency, and decreasing reliance on the hospital network). Wireless network 160-1 may include interfaces for WPAN connections and communication with external WPAN (e.g., Bluetooth) devices such as audio devices, smart instruments, robotic instruments, sensors, etc.

Peripheral interfaces 680 may include standard interfaces such as USB, which may provide connectivity to OR cameras, provide power, and support surgical instruments such as surgical shears, sealers, etc. Custom interfaces 683 may include interfaces specific to a manufacturer such as for insufflation devices, couplings for electro-mechanical devices such as pumps, aspirators, irrigators, etc. (not shown in FIG. 6).

Figure 7:
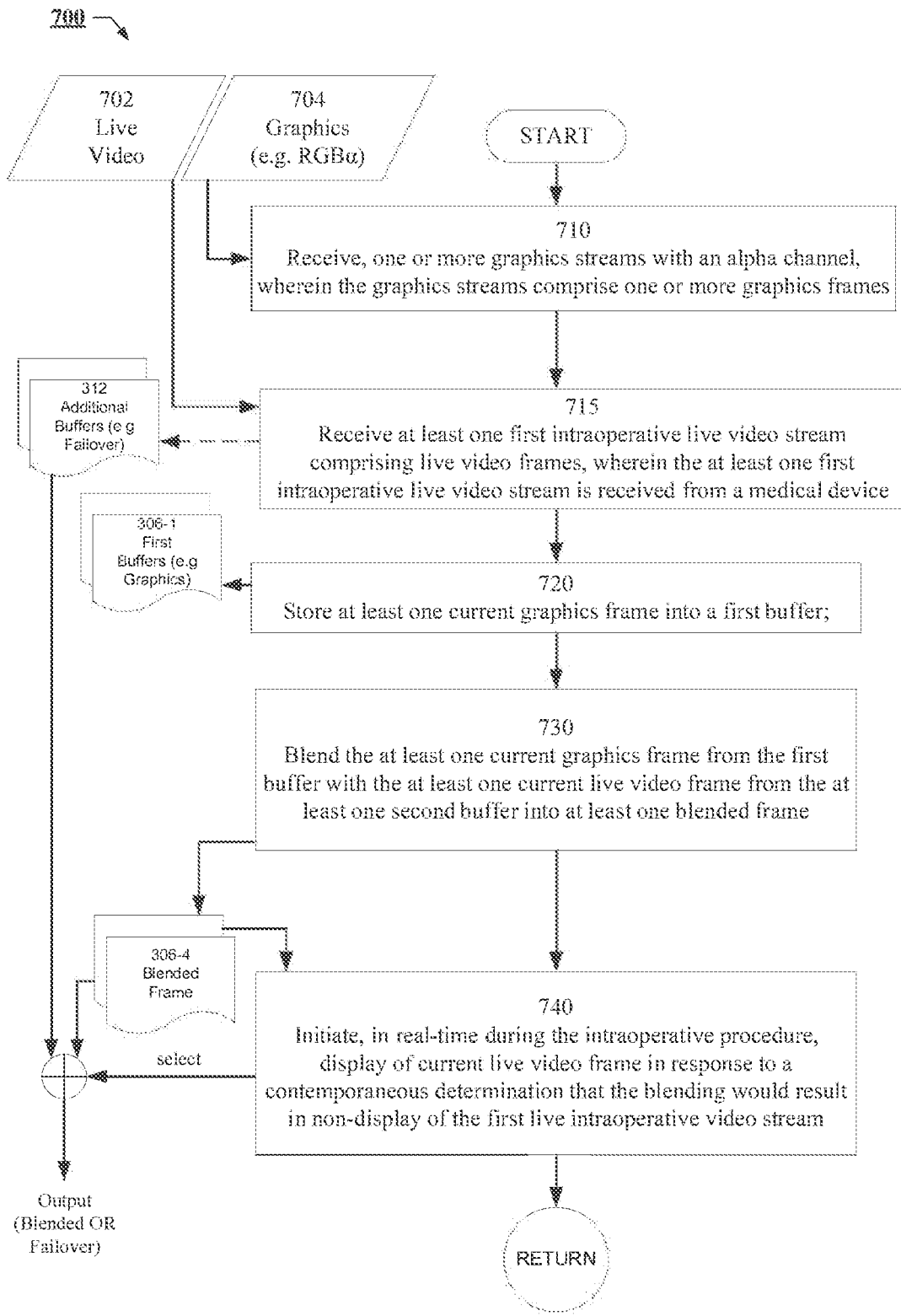
FIG. 7 shows a flowchart of an example method to facilitate fault-tolerant intraoperative visualization in accordance with certain embodiments disclosed herein.

FIG. 7 shows an exemplary flowchart of a method 700 for fault-tolerant intraoperative visualization. In some embodiments, method 700 may be performed on a computing device (such as hub 150). In some embodiments, method 700 may be performed by some combination FPE 225, GPU 220, and/or processor 250. Method 700 may be implemented by some combination of hardware, software, and firmware. As one non-limiting example, method 700 may be implemented using an add-on M2 expansion card with a PCIe interface to add fault-tolerant intraoperative visualization functionality an existing intraoperative computing device.

In block 710, one or more graphics streams 704, which include an alpha channel, may be received. The graphics streams 704 may comprise one or more graphics frames. In some embodiments, the one or more graphics streams may include a pre-multiplied alpha channel.

In block 715, at least one first intraoperative live video stream 702 comprising live video frames may be received, wherein the at least one first intraoperative live video stream 702 may be received from a medical device (e.g., endoscope 670-1, ultrasound 670-2, etc. during a medical procedure). As one example, live video stream 702 may be one of live video streams 208 and/or 209 and graphics stream 704 may correspond to graphics (UI) stream 222. In some embodiments, the at least one first intraoperative live video stream 702 may be obtained by mixing two intraoperative live video streams (e.g., 202-1 and 202-2). For example, cross-channel mixing may be used to obtain the at least one first intraoperative live video stream. In some embodiments, the at least one first intraoperative live video stream 702 may comprise a stereoscopic live video stream (e.g., 3D live video stream 208).

In block 720, at least one current graphics frame may be stored into a first buffer (e.g., frame buffers 306-1).

In block 730, the at least one current graphics frame from the first buffer (e.g., 306-1) may be blended with the at least one current live video frame from the at least one second buffer (e.g., 306-2) to obtain at least one blended frame. In some embodiments, the blending may be performed in real-time and the output may be stored in blended frame buffers 306-4. In some embodiments, blending operations may be performed in parallel using multiple processors or processing cores.

In block 740, display of current live video frame from the at least one additional buffer (e.g., failover buffers 312) may be initiated in real-time and during the intraoperative procedure, in response to a contemporaneous determination that the blending would result in non-display of the first live intraoperative video stream. For example, upon determining that the blending would result in the current live video being obscured or not being visible, the display of current live video frame from the failover buffers 312 may be enabled. In some embodiments, the determination to initiate display of the current live video frame from the at least one third buffer may occur within the time to complete the blending of the at least one current graphics frame with the at least one current live video frame.

In some embodiments, the at least one current live video frame may be stored into at least one second buffer and at least one third buffer (e.g., failover buffers 312). In some embodiments, the at least one current live video frame may be downsampled and the at least one downsampled current live video frame may be stored in to the at least one third buffer. In some embodiments, the downsampling may be performed in real-time.

In some embodiments, in block 740, the determination to initiate display of the at least one current live video frame from the at least one third buffer may be based on a ratio of a number of solid lines in the at least one blended frame to a total number of lines in the at least one blended frame. For example, the determination to initiate display of the at least one current live video frame from the at least one third buffer may be made when the ratio exceeds a threshold.

In some embodiments, the method may further comprise displaying, in real time, the at least one current live video frame from the at least one third buffer along with an error indication (e.g., error indication 555).

In some embodiments, method 700 may further comprise (e.g., after block 740) initiating display of the at least one blended frame, in response to a determination that the blending would result in display of the at least one first live intraoperative video stream. For example, in some embodiments, display of the at least one blended frame may be a "default" mode so that the blended frame is displayed when display of the live video stream is not impaired. In instances where blending would result in the current live video being obscured or not being visible (e.g., as determined in block 740), the display of current live video frame from the failover buffers 312 may be enabled. For example, the determination to initiate display of the at least one blended frame may be made when the ratio of a number of solid lines in the at least one blended frame to a total number of lines in the at least one blended frame is below a threshold.

Although the present disclosure is described in connection with specific embodiments for instructional purposes, the disclosure is not limited thereto. Various adaptations and modifications may be made to the disclosure without departing from the scope. Therefore, the spirit and scope of the appended claims should not be limited to the foregoing description.

What is claimed is:

1. A method comprising:
displaying, during an intraoperative procedure, a blended live video stream that comprises a graphics window in a first portion of at least one video frame of a plurality of video frames of a live video stream captured by a camera, wherein the live video stream comprises a surgical scene within an entirety of each of the video frames captured by the camera;
determining, while the blended live video stream is displayed, that a second portion of a video frame of the plurality of video frames that is to be displayed is at least partially obscured; and
responsive to determining that the second portion of the video frame is at least partially obscured, displaying the live video stream captured by the camera instead of the blended live video stream.

2. The method of claim 1 further comprising producing the blended live video stream by blending a frame that comprises the graphics window with the at least one video frame of the plurality of video frames of the live video stream.

3. The method of claim 1, wherein displaying the live video stream comprises displaying one or more downsampled versions of one or more video frames of the plurality of video frames of the live video stream on a display.

4. The method of claim 3 further comprising displaying an error message in an area of the display that is not being used to display the one or more downsampled versions of the one or more video frames.

5. The method of claim 1, wherein determining that the second portion of the video frame that is to be displayed is at least partially obscured comprises determining that the video frame comprises one or more solid lines.

6. The method of claim 5, wherein the blended live video stream comprises a blended frame that includes the graphics window and the video frame, wherein the live video stream is displayed responses to a ratio of a number of the one or more solid lines divided by a total number of lines in the blended frame is greater than a threshold.

7. The method of claim 1, wherein the live video stream comprises a stereoscopic live video stream.

8. A system comprising:
a display;
at least one processor; and
memory having instructions which when executed by the at least one processor causes the system to:
display, during an intraoperative procedure, a blended live video stream on the display, the blended live video stream comprises a graphics window in a first portion of at least one video frame of a plurality of video frames of a live video stream captured by a camera, wherein the live video stream comprises a surgical scene within an entirety of each of the video frames captured by the camera;
determine, while the blended live video stream is displayed, that a second portion of a video frame of the plurality of video frames that is to be displayed is at least partially obscured; and
responsive to determining that the second portion of the video frame is at least partially obscured, display the live video stream captured by the camera instead of the blended live video stream on the display.

9. The system of claim 8, wherein the memory comprises further instructions to produce the blended live video stream by blending a graphics frame that comprises the graphics window with the at least one video frame of the plurality of video frames of the live video stream.

10. The system of claim 8, wherein displaying the live video stream comprises displaying one or more downsampled versions of one or more video frames of the plurality of video frames of the live video stream on the display.

11. The system of claim 10, wherein the memory comprises further instructions to display an error message in an area of the display that is not being used to display the one or more downsampled versions of the one or more video frames.

12. The system of claim 8, wherein determining that the second portion of the video frame that is to be displayed is at least partially obscured comprises determining that the video frame comprises one or more solid lines.

13. The system of claim 12, wherein the blended live video stream comprises a blended frame that includes the graphics window and the video frame, wherein the live video stream is displayed responses to a ratio of a number of the one or more solid lines divided by a total number of lines in the blended frame is greater than a threshold.

14. The system of claim 8 comprises a stereoscopic camera, wherein the memory has further instructions to receive a stereoscopic live video stream as the live video stream.

15. A non-transitory machine-readable medium comprising instructions to configure at least one processor to:
display, during an intraoperative procedure, a blended live video stream on a display, the blended live video stream comprises a graphics window in a first portion of at least one video frame of a plurality of video frames of a live video stream captured by a camera;
determine, while the blended live video stream is displayed, that a second portion of a video frame of the plurality of video frames that is to be displayed is at least partially obscured; and
responsive to determining that the second portion of the video frame is at least partially obscured, display, on the display, the live video stream without blending video or graphics information on the plurality of video frames on the display.

16. The non-transitory machine-readable medium of claim 15 comprises further instructions to configure the at least one processor to produce the blended live video stream by blending a graphics frame that comprises the graphics window with the at least one video frame of the plurality of video frames of the live video stream.

17. The non-transitory machine-readable medium of claim 15, wherein displaying the live video stream comprises displaying one or more downsampled versions of one or more video frames of the plurality of video frames of the live video stream on the display.

18. The non-transitory machine-readable medium of claim 17 comprises further instructions to display an error message in an area of the display that is not being used to display the one or more downsampled versions of the one or more video frames.

19. The non-transitory machine-readable medium of claim 15, wherein determining that the second portion of the video frame that is to be displayed is at least partially obscured comprises determining that the video frame comprises one or more solid lines.

20. The non-transitory machine-readable medium of claim 19, wherein the blended live video stream comprises a blended frame that includes the graphics window and the video frame, wherein the live video stream is displayed responses to a ratio of a number of the one or more solid lines divided by a total number of lines in the blended frame is greater than a threshold.

\* \* \* \* \*